Figure 1:
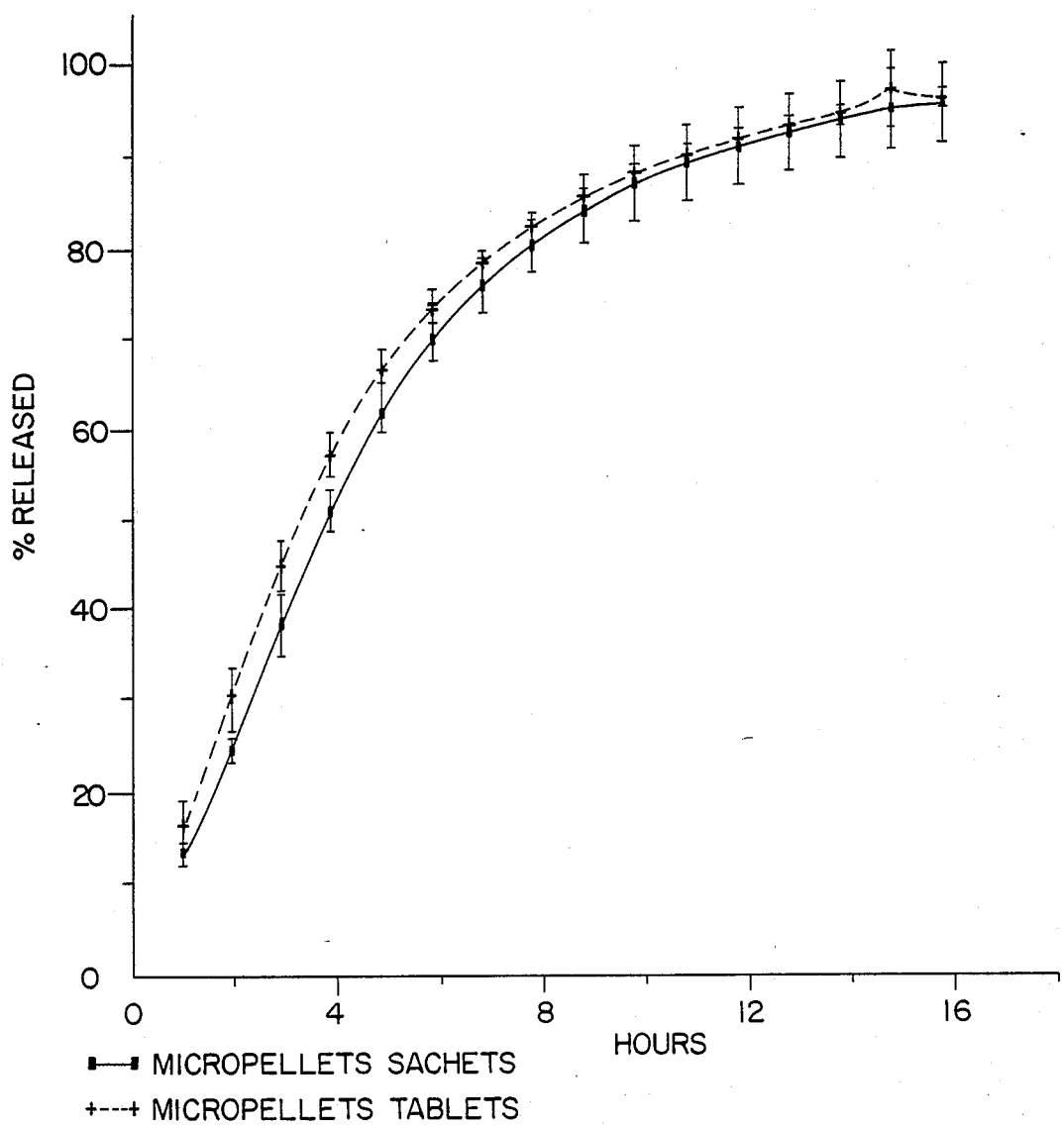

United States Patent [19]

Ventouras

[11] Patent Number: 4,886,669
[45] Date of Patent: Dec. 12, 1989

[54] GALENICAL FORMULATION

[75] Inventor: Kimon Ventouras, Le Lignon, Switzerland

[73] Assignee: Zyma SA, Nyon, Switzerland

[21] Appl. No.: 125,604

[22] Filed: Nov. 25, 1987

[30] Foreign Application Priority Data

Nov. 27, 1986 [GB] United Kingdom ............ 8628359

[51] Int. Cl.$^4$ .................................. A61K 9/26
[52] U.S. Cl. ............................. 424/469; 424/470; 424/493; 424/494; 424/496; 424/497
[58] Field of Search ............ 424/465, 469, 466, 470, 424/493, 494, 496, 497

[56] References Cited

U.S. PATENT DOCUMENTS

| | | | |
|---|---|---|---|
| 3,558,768 | 1/1971 | Klippel | 424/496 X |
| 3,974,272 | 8/1976 | Polli et al. | 424/78 |
| 4,017,598 | 4/1977 | Ohno et al. | 424/35 |
| 4,189,469 | 2/1980 | Gleixner et al. | 424/80 |
| 4,321,253 | 3/1982 | Beatty | 424/35 |
| 4,540,602 | 9/1985 | Motoyama et al. | 424/496 X |
| 4,555,399 | 11/1985 | Hsiao | 424/465 |
| 4,609,675 | 9/1986 | Franz | 514/781 X |
| 4,666,703 | 5/1987 | Kopf | 424/470 |
| 4,681,759 | 7/1987 | Porobcan | 424/80 |
| 4,695,591 | 9/1987 | Hanna et al. | 424/493 X |
| 4,754,027 | 6/1988 | Applegren | 424/496 X |
| 4,755,385 | 7/1988 | Etienne et al. | 424/465 X |
| 4,755,386 | 7/1988 | Hsiao | 424/435 |

FOREIGN PATENT DOCUMENTS

| | | |
|---|---|---|
| 0052076 | 5/1982 | European Pat. Off. . |
| 0181966 | 5/1986 | European Pat. Off. . |
| WO86/04817 | 8/1986 | PCT Int'l Appl. . |
| WO86/06626 | 11/1986 | PCT Int'l Appl. . |
| 2082539 | 3/1982 | United Kingdom . |
| 2086725 | 5/1982 | United Kingdom . |

Primary Examiner—Thurman K. Page
Attorney, Agent, or Firm—Wenderoth, Lind & Ponack

[57] ABSTRACT

A water-dispersible tablet essentially consisting of
(a) microparticles which contain at least one pharmaceutically active substance
(b) a least one disintegrant and
(c) a swellable material, which is able to generate a high viscosity when coming into contact with water;

which disintegrates rapidly in water thus forming a homogeneous suspension of high viscosity that can easily be swallowed, is disclosed. It is prepared by methods known per se.

20 Claims, 1 Drawing Sheet

GALENICAL FORMULATION

The present invention relates to an improved tablet which contains at least one pharmaceutically active substance and rapidly disintegrates in contact with water so as to generate a viscous, homogeneous suspension. The dispersion formed after contact with water can be swallowed easily by any person who is in need of the pharmaceutically active substance(s).

This route of administration of pharmaceutically active substances is particularly advantageous, when a relatively large single dose must be applied orally, since a tablet or another shaped form, e.g. a capsule, would be too voluminous for oral intake. Also in cases where no particularly large single dose must be applied, the route of administration described above can be advantageous, because it is more convenient especially for children and elderly people, and other people too, who often have troubles swallowing medicines in solid form, such as tablets or other shaped forms. Furthermore, there are certain drugs, where multiple unit dosage forms are particularly advantageous to overcome a local irritation of the gastrointestinal tract after peroral administration, e.g. non-steroidal antiinflammatory drugs, such as ibuprofen, or other drugs, e.g. potassium chloride or sodium fluoride.

Rapidly disintegrating tablets are known in the art, e.g. from EP-A-52076 or WO-A-86/04817:

However, the known tablets suffer from the following disadvantages: After disintegration, they form a dispersion containing the isolated—mostly coated—microparticles. Even in those cases where the microparticles used are of small size—e.g. of 0.3 to 0.6 mm diameter—, when swallowed, they are perceived as individual grains in the mouth in an unpleasant manner and may be caught on the spaces between the teeth. Generally spoken, the dispersion prepared from such tablets produces a certain feeling of hoarseness in the mouth.

Furthermore, often liquid foods, e.g. apple sauce or marmalade, are needed to administer the tablets known in the art. The use of the latter has the following disadvantages: (1) The person in need of the drug always has to take in food simultaneously when swallowing a formulation of the invention. But food intake can often be completely undesired in such situations, e.g. for reason of avoiding increase of weight. (2) Drug absorption may be influenced by the food taken in simultaneously in an undesired manner.

It is the aim of the present invention to avoid these disadvantages and to present a tablet which disintegrates in water to a perfectly homogeneous dispersion, in which, when taken up by mouth and swallowed, no individual grains can be perceived any more. Furthermore, this goal is to be achieved without the need of any liquid foods.

Thus, the present invention relates to a water-dispersible tablet essentially consisting of
(a) microparticles which contain at least one pharmaceutically active substance
(b) at least one disintegrant and
(c) a swellable material, which is able to generate a high viscosity when coming into contact with water;
which disintegrates rapidly in water thus forming a homogeneous suspension of high viscosity that can easily be swallowed.

The microparticles (a) can be coated microparticles, a mixture of coated and uncoated microparticles, or uncoated microparticles, preferably such with controlled release or taste masking properties. The coated microparticles, the use of which is preferred, consist of a granule or crystal of a pharmaceutically active substance, which is coated or encapsulated by any material which is known in the art to be suitable for the intended purpose, e.g. by polymeric materials dissolved in organic solvents or dispersed in water as latex. The intended purpose of the coating may be e.g. the control of the release of a certain pharmaceutically active compound as well-known in the art, or the masking of any undesired, e.g. bitter, taste of such a compound. The polymeric material mentioned above can be applied either alone or in admixture with other insoluble or soluble polymers. Moreover, the coating may contain e.g. plasticizers, glidants and/or flavours.

Also uncoated microparticles may exhibit control release properties, e.g. in case the substance used is only very poorly soluble in water.

The size of the microparticles used is e.g. 0.2 to 1.0 mm diameter, preferably 0.3 to 0.8 and especially 0.3 to 0.5 mm diameter.

As pharmaceutically active substances used in the tablet of the invention come into consideration all those which are suitable for peroral administration. This applies for example for (a) potassium chloride administered e.g. in the treatment of hypokaliaemia, (b) lithium salts administered e.g. in psychotherapy, (c) non-steroidal antiinflammatory drugs, e.g. ibuprofen, (d) calcium salts e.g. in the therapy of hypocalcemic states or for calcium supplementation, (e) sodium fluoride e.g. in the treatment of osteoporosis, (f) pridinol, or a salt thereof, e.g. as a muscle relaxant, (g) dimethindene, or a salt thereof, e.g. as an antihistaminicum, (h) methyl-xanthines, e.g. proxyphylline, diprophylline and/or theophylline, e.g. as bronchodilators, (i) a mixture of O-$\beta$-hydroxy-ethyl-rutosides (Venoruton®) e.g. in the treatment of venous diseases, (j) antitussive drugs, e.g. butamirate or a salt thereof, such as butamirate citrate, codeine or a derivative thereof, or noscapine, (k) antipyretics, e.g. acetaminophen, (l) vitamines or multivitamines preparations, (m) cardiovascular and vascular drugs, such as all the betablockers known in the art, or e.g. 1-O-ethyl-3-O-propyl-5,6-di-O-(4-chlorobenzyl)-D-glucofuranoside, (n) drugs especially used against elderlys' or childrens' diseases (geriatric or pediatric drugs), e.g. pyrisuccideanol or a salt thereof, such as pyrisuccideanol dimaleate, ticlopidine, dipyridamole or diazepam, (o) drugs useful to balance the hydroelectrolytes e.g. for the treatment of diarrhoea, e.g. sodium or potassium salts, (p) antibiotic drugs, e.g. erythromycin or a salt thereof or doxycycline or a salt thereof, or (q) nootropica, e.g. piracetam. All the salts mentioned above must of course be pharmaceutically acceptable so as to be used in the formulations of the invention.

The disintegrant (b) is preferably crospovidone (a cross-linked homopolymer of N-vinyl-2-pyrrolidone) known e.g. under the trade names Polyplasdone-XL® (supplied by GAF Corp., New York, USA) and Kollidon-CL®. But other known disintegrants, e.g. sodium starch glykolate (e.g. Primojel®, Explotab®), sodium croscarmellose (a cross-linked polymer of carboxymethylcellulose sodium), e.g. Ac-di-sol® (supplied by FMC Corp., Philadelphia, USA), starches or anionic or cationic resins, can also be useful as disintegrants.

The swellable material (c) is preferably guar gum, e.g. Meyprogat®-150, supplied by Meyhall Chem., Kreuzlingen (Switzerland), especially in granulated form, but may be also any other swellable material allowed for human administration. It may be a naturally occurring or a chemically obtained polymer. Examples for useful swellable materials are xanthan gum, alginates, dextran, pectins, pregelatinized starches, polysaccharides, cellulose derivatives such as sodium or calcium carboxymethylcellulose, hydroxypropylcellulose or hydroxypropylmethylcellulose.

In order to promote disintegration and to avoid a swelling of the swellable material (c) which is too rapid and thus would prevent the disintegration at all, other additives well-known in the art can be also incorporated into the tablet. These can be for example electrolytes, i.e. compounds forming species in water which carry a charge, e.g. ionic substances, such as sodium chloride. As further examples, acids, especially organic acids, e.g. citric acid, and bases, such as sodium hydrogen carbonate, can be mentioned. Furthermore, compounds forming no ions in water are suitable for the intended purpose, e.g. sugars, such as sorbitol.

The tablets of the invention may also contain auxiliaries customarily used for tabletting production, e.g. fillers, binders, lubricants, antisticking agents and flavours.

Rapid disintegration in water means e.g. such within two minutes, preferably such within one minute and especially such in less than one minute.

High viscosity of the homogeneous suspension formed means e.g. an apparent viscosity at 20° C. of 30 to 3000 mPa.s, preferably of 30 to 1000 mPa.s, more preferably of 100 to 600 mPa.s and especially of 150 to 500 mPa.s (Brookfield viscosimeter).

The underlying principle of this particular pharmaceutical composition, which is the generation of a homogeneous suspension from a water-dispersible tablet, can be summarized as follows: Coming into contact with water, the tablet of the invention disintegrates rapidly, generally in less than one minute, owing to the disintegrant involved, which surpasses the opposite swelling effect caused by the swellable material. After the tablet has disintegrated in water, the swellable material swells with the result, that its macromolecules dispersed in water generate a viscous, homogeneous suspension consisting of the micropellets and all the auxiliaries included. It is evident that the distance between the particles of the swellable material, e.g. guar gum, within the tablet is very important, because complete disintegration of the tablet has to take place before the swelling of the swellable material prevents the disintegration. For example, if instead of granulated guar gum, a normally fine powder of guar gum is used in the tablet formulation of Example 1, a voluminous hydrophilic matrix tablet impossible to be swallowed is formed in the water due to the guar gum present. But, of course, also the normally fine powder of guar gum can be used successfully in a formulation according to the invention. For doing so, e.g. larger amounts of the additives mentioned above for promoting disintegration and avoiding a too rapid swelling of the swellable material have to be applied so as to reduce the rate of swelling of the guar gum.

A mixture of the components (a) and (c) of the tablet of the invention in the form of a powder, a granulate and/or e.g. coated microparticles is similarly useful as the tablet itself. Such a mixture can e.g. be packed in sachets for reconstitution with water for single dose oral administration, see Example 2. Such mixtures form another embodiment of the instant invention.

The tablets of the invention can be produced in a manner known per se by compressing the intimately mixed components of the tablet in a usual tablet-compressing machine. For sachet preparation, the intimately mixed components are filled into sachets, and then the sachets are closed in a manner known per se.

The following examples are intended to illustrate the invention and are not to be construed as being limitations thereon. Temperatures are given in degrees Centigrade.

EXAMPLE 1

Water-dispersible micropellets tablets (for preparing extemporaneous suspensions) of methyl-xanthines—with particularly good organoleptic properties for the administration to elderly people and children—are obtained by tabletting a suitable mixture of (a) coated micropellets containing the methyl-xanthines, (b) granules of acidified guar gum and (c) dry granules.

(a) Approximately 1 kg of micropellets, size 0.3–0.5 mm, of methylxanthines are prepared according to the following formula and process:

A mixture of powders of 330 g proxyphylline, 330 g diprophylline, 220 g anhydrous theophylline, 30 g Prejel®-PA-5 (pregelatinized slightly oxidized potato starch, supplied by AVEBE, Weendam, Netherlands) and 50 g Avicel®-PH-105 (microcrystalline cellulose, particle size 20μ, supplied by FMC Corporation, Philadelphia, USA) is prepared in a planetary mixer (Erweka) during about 15 minutes. This mixture is humidified with a mixture of 10 g silicone emulsion, 40 g Eudragit®-NE30D (a 30% aqueous dispersion of an ethyl acrylate/methyl methacrylate copolymer 70:30 having a molecular weight of about 800 000 supplied by Röhm Pharma, Darmstadt, FRG) and 60 g of Aquacoat®-ECD-30 [ethylcellulose, as a 30% aqueous polymeric dispersion having a low particle size (latex form) and a narrow particle-size distribution, supplied by FMC Corporation, Philadelphia, USA] in 20 g of water. This mass is kneaded for about 5 minutes and then extruded through a screen with holes size of 0.5 mm diameter (apparatus Fuji Paudal EXKS-1). The extruded mass is spheronised in a marumerizer Q-230 with a speed of 900 rpm for 30 seconds.

The micropellets obtained are dried for 20 minutes at 50°. 300 g of these micropellets are coated in a fluidised-bed (Aeromatic Strea-1) in a co-current technique with a suspension mixture of 214 g Eudragit®-NE30D and 36 g of Aquacoat®-ECD-30. The spray rate of the coating suspension is 5 g/minute and the inlet air temperature is 45°. The coated micropellets are treated in the fluidised-bed for 2 hours at 70° and then cooled with air at 22°.

(b) Approximately 400 g granules of acidified guar gum are prepared in a fluidised-bed (Aeromatic Strea-1) in a co-current technique. On a mixture of 320 g Meyprogat®-150 (guar gum) and 60 g lactose powder, a solution of 20 g citric acid in 350 g water is sprayed. The spray rate of the solution is 10 g/minute and the inlet air temperature is 45°.

(c) Approximately 2 kg of dry granules are prepared by tabletting a mixture of powders of 756 g Avicel®-PH-105, 360 g Avicel®-PH-101 (microcrystalline cellulose, particle size 50μ, supplied by FMC Corporation, Philadelphia, USA), 300 g Polyplasdone®-XL, 360 g Tablettose® (lactose in mirogranular form for direct compression, supplied by Meggle, Reitmehring, FRG), 90 g talcum, 6 g Aerosil®-200 (pyrolytically manufactured silicic acid ≙ $SiO_2$, supplied by Degussa, Frankfurt, FRG), 6 g magnesium stearate and 6 g of saccharine-sodium in a press (KORSCH-EKO) with punches of 20 mm diameter.

Tablets of 1.3 g weight are obtained, which are then screened into a granular shape by forcing them through a screen of 4 mm and further 1 mm size.

Water-dispersible controlled-release methyl-xanthines tablets are obtained by tabletting in a KORSCH-EKO press a mixture of 650 g coated micropellets of methyl-xanthines (a), 275 g of acidified guar gum granules (b), 785 g of dry granules (c), 35 g of powdered banana flavour, 1.25 g magnesium stearate and 1.25 g of Aerosil®-200. The tablets obtained are characterised by a weight of 3495 mg with a coefficient variation of 1.4%, a hardness of 100N, a diameter of 25 mm and a dispersion time to obtain an extemporaneous suspension in a cup of water of approximately 1 minute.

EXAMPLE 2

A similar process as described in example 1 is used to obtain a dry suspension of the same methyl-xanthines micropellets in sachets:

| Composition | | |
|---|---|---|
| Coated micropellets, size 0.3–0.5 mm, containing methyl-xanthines | 1300 mg | |
| Avicel®-PH-101 | 344 mg | |
| Avicel®-PH-105 | 722 mg | |
| Tablettose® | 344 mg | |
| Banana flavour powder | 100 mg | dry granulation |
| Saccharine-Na | 5.7 mg | |
| Magnesium stearate | 5.7 mg | |
| Aerosil®-200 | 5.7 mg | |
| Talcum | 86 mg | |
| Meyprogat®-150 | 680 mg | wet granulation |
| Lactose powder | 120 mg | |
| total | ≈ 3713.1 mg | |

The percentage of release "in vitro" of the methylxanthines from the water-dispersible micropellets tablets (example 1) and the sachets (example 2) is presented in FIG. 1.

EXAMPLE 3

(a) Microparticles of a mixture of O-β-hydroxyethyl-rutosides (Venoruton®) are prepared by wet granulation in a fluidised-bed (Aeromatic S-2, 10 bar). Approximately 8 kg of granules are obtained by wet granulation of 6 kg O-β-hydroxyethyl-rutosides and 1.116 kg of Prejel®-PA-5 with a solution of 0.753 kg O-β-hydroxyethyl-rutosides in 2.8 kg of water in a fluidised-bed with the counter-current technique. The spray rate of the solution is 40 g/minute, the inlet air temperature is 40° and the inlet air flow is 280 m³/hour. At the end, these granules are dried in the fluidised-bed.

Microgranules of 0.2–0.5 mm are collected by sieving, and 400 g of these particles are coated in a fluidised-bed (Aeromatic Strea-1) in a co-current technique with a dispersion mixture of 228 g Eudragit®-NE30D and 39 g Aquacoat®-ECD-30. The spray rate of coating is 5 g/minute and the inlet air temperature is 40°. At the end, there is also a spray-on with a solution of 40 g Aquacoat®-ECD-30 in 20 g water. The coated microparticles are dried for 10 minutes at 40°. Then they are treated in the fluidised-bed for 2 hours at 70° and finally cooled with air of 22°.

(b) Water-dispersible tablets containing a mixture of O-β-hydroxy-ethyl-rutosides are obtained as follows:

61.6 g of the heat-treated coated microparticles containing a mixture of O-β-hydroxyethyl-rutosides (obtained in Example 3a), 20 g Avicel®-PH-105, 12 g Polyplasdone®-XL, 16 g Sorbex®-RP/F (sorbitol), 20 g of the previously described acidified granular guar gum (see Example 1b), 0.6 g magnesium stearate, 0.2 g sodium saccharine and 4 g citron flavour powder are mixed.

With the help of a hydraulic tablet press (SPECAC) and punches of 25 mm diameter with bevelled edges, this mixture is transformed into tablets of 7.6 mm thickness and 3361 mg weight. The hardness of these tablets is about 60 Newton. The disintegration and dispersion in a glass of water at room temperature is approximately 1 minute.

I claim:
1. A water-dispersible tablet comprising
   (a) microparticles which contain at least one pharmaceutically active substance
   (b) at least one disintegrant and
   (c) a swellable material which is able to generate a high viscosity when coming into contact with water and which is selected from the group consisting of guar gum, xanthan gum, alginates, dextran, pectins, polysaccharides, sodium or calcium carboxymethylcellulose, hydroxypropylcellulose and hydroxypropylmethylcellulose;
which tablet disintegrates rapidly in water forming a homogeneous suspension of high viscosity that can easily be swallowed.

2. A water-dispersible tablet according to claim 1, which contains coated microparticles.

3. A water-dispersible tablet according to claim 2, which contains coated microparticles of 0.3 to 0.8 mm diameter.

4. A water-dispersible tablet according to claim 3, which contains guar gum as the swellable material.

5. A water-dispersible tablet according to claim 1, which contains granulated guar gum as the swellable material.

6. A water-dispersible tablet according to claim 4, which contains granulated guar gum as the swellable material.

7. A water-dispersible tablet according to claim 4, which contains crospovidone as the disintegrant.

8. A water-dispersible tablet according to claim 6, which contains crospovidone as the disintegrant.

9. A water-dispersible tablet according to claim 1, which disintegrates in water within one minute.

10. A water-dispersible tablet according to claim 4, which disintegrates in water within one minute.

11. A water-dispersible tablet according to claim 5, which disintegrates in water within one minute.

12. A water-dispersible tablet according to claim 8, which disintegrates in water within one minute.

13. A water-dispersible tablet according to claim 9, which forms, in water, a homogeneous suspension with an apparent viscosity at 20° C. of 30 to 1000 mPa.s.

14. A water-dispersible tablet according to claim 10, which forms, in water, a homogeneous suspension with an apparent viscosity at 20° C. of 30 to 1000 mPa.s.

15. A water-dispersible tablet according to claim 11, which forms, in water, a homogeneous suspension with an apparent viscosity at 20° C. of 30 to 1000 mPa.s.

16. A water-dispersible tablet according to claim 12, which forms, in water, a homogeneous suspension with an apparent viscosity at 20° C. of 30 to 1000 mPa.s.

17. A water-dispersible tablet according to claim 7, which contains as the pharmaceutically active substance(s) a member of the group consisting of drugs for the treatment of hypokaliaemia, psychotherapy drugs, non-steroidal antiinflammatory drugs, drugs for the therapy of hypocalcemic states or for calcium supplementation, drugs for the treatment of osteoporosis, muscle relaxants, antihistaminica, bronchodilators, drugs for the treatment of venous diseases, antitussive drugs, antipyretics, vitamins, cardiovascular and vascular drugs, geriatric drugs, pediatric drugs, drugs useful to balance the hydroelectrolytes, antibiotic drugs and nootropica.

18. A water-dispersible tablet according to claim 13, which contains as the pharmaceutically active substance(s) a member of the group consisting of drugs for the treatment of hypokaliaemia, psychotherapy drugs, non-steroidal antiinflammatory drugs, drugs for the therapy of hypocalcemic states or for calcium supplementation, drugs for the treatment of osteoporosis, muscle relaxants, antihistaminica, bronchodilators, drugs for the treatment of venous diseases, antitussive drugs, antipyretics, vitamins, cardiovascular and vascular drugs, geriatric drugs, pediatric drugs, drugs useful to balance the hydroelectrolytes, antibiotic drugs and nootropica.

19. A water-dispersible tablet according to claim 14, which contains as the pharmaceutically active substance(s) a member of the group consisting of drugs for the treatment of hypokaliaemia, psychotherapy drugs, non-steroidal antiinflammatory drugs, drugs for the therapy of hypocalcemic states or for calcium supplementation, drugs for the treatment of osteoporosis, muscle relaxants, antihistaminica, bronchodilators, drugs for the treatment of venous diseases, antitussive drugs, antipyretics, vitamins, cardiovascular and vascular drugs, geriatric drugs, pediatric drugs, drugs useful to balance the hydroelectrolytes, antibiotic drugs and nootropica.

20. A water-dispersible tablet according to claim 15, which contains as the pharmaceutically active substance(s) a member of the group consisting of drugs for the treatment of hypokaliaemia, psychotherapy drugs, non-steroidal antiinflammatory drugs, drugs for the therapy of hypocalcemic states or for calcium supplementation, drugs for the treatment of osteoporosis, muscle relaxants, antihistaminica, bronchodilators, drugs for the treatment of venous diseases, antitussive drugs, antipyretics, vitamins, cardiovascular and vascular drugs, geriatric drugs, pediatric drugs, drugs useful to balance the hydroelectrolytes, antibiotic drugs and nootropica.

* * * * *